(12) United States Patent
Saltel et al.

(10) Patent No.: US 8,999,393 B1
(45) Date of Patent: Apr. 7, 2015

(54) SUSTAINED RELEASE FORMULATIONS OF LORAZEPAM

(71) Applicants: Douglas A. Saltel, Austin, TX (US); Michael Vachon, Quebec (CA)

(72) Inventors: Douglas A. Saltel, Austin, TX (US); Michael Vachon, Quebec (CA)

(73) Assignee: Edgemont Pharmaceuticals LLC, Austin, TX (US)

( * ) Notice: Subject to any disclaimer, the term of this patent is extended or adjusted under 35 U.S.C. 154(b) by 0 days.

(21) Appl. No.: 14/150,375

(22) Filed: Jan. 8, 2014

Related U.S. Application Data

(60) Provisional application No. 61/750,797, filed on Jan. 9, 2013, provisional application No. 61/762,833, filed on Feb. 8, 2013.

(51) Int. Cl.
*A61K 9/14* (2006.01)
*A61K 9/50* (2006.01)

(52) U.S. Cl.
CPC ............ *A61K 9/5047* (2013.01); *A61K 9/5026* (2013.01)

(58) Field of Classification Search
None
See application file for complete search history.

(56) References Cited

U.S. PATENT DOCUMENTS

| | | | |
|---|---|---|---|
| 3,296,249 A | 1/1967 | Bell | |
| 3,786,813 A | 1/1974 | Michaels | |
| 3,845,770 A | 11/1974 | Theeuwes et al. | |
| 4,361,545 A | 11/1982 | Powell et al. | |
| 4,361,546 A | 11/1982 | Stricker et al. | |
| 4,624,847 A | 11/1986 | Ayer et al. | |
| 4,794,001 A | 12/1988 | Mehta et al. | |
| 4,839,177 A | 6/1989 | Colombo et al. | |
| 5,009,895 A | 4/1991 | Lui | |
| 5,273,758 A | 12/1993 | Royce | |
| 5,275,824 A | 1/1994 | Carli et al. | |
| 5,326,570 A | 7/1994 | Rudnic et al. | |
| 5,354,556 A | 10/1994 | Sparks et al. | |
| 5,567,441 A | 10/1996 | Chen | |
| 5,795,882 A * | 8/1998 | Bishop et al. | 514/170 |
| 5,871,776 A | 2/1999 | Mehta | |
| 5,912,013 A | 6/1999 | Rudnic et al. | |
| 5,945,125 A | 8/1999 | Kim | |
| 6,312,728 B1 | 11/2001 | Beiman et al. | |
| 6,348,469 B1 | 2/2002 | Seth | |
| 6,500,459 B1 * | 12/2002 | Chhabra et al. | 424/474 |
| 6,555,136 B2 * | 4/2003 | Midha | 424/469 |
| 6,663,888 B2 | 12/2003 | Percel et al. | |
| 6,699,503 B1 | 3/2004 | Sako et al. | |
| 6,703,045 B2 | 3/2004 | Dhawan et al. | |
| 7,153,497 B2 | 12/2006 | Hughes et al. | |
| 7,195,778 B2 | 3/2007 | Fleshner-Barak et al. | |
| 7,670,627 B2 | 3/2010 | Shefer et al. | |
| 7,976,871 B2 | 7/2011 | Vaya et al. | |
| 8,231,897 B2 | 7/2012 | MacGregor | |
| 8,277,840 B2 | 10/2012 | Joshi et al. | |
| 8,460,710 B2 * | 6/2013 | Burnside et al. | 424/490 |
| 2003/0044458 A1 * | 3/2003 | Wright et al. | 424/458 |
| 2003/0050620 A1 * | 3/2003 | Odidi et al. | 604/890.1 |
| 2003/0180362 A1 * | 9/2003 | Park et al. | 424/470 |
| 2004/0028729 A1 | 2/2004 | Shojaei et al. | |
| 2005/0031688 A1 * | 2/2005 | Ayala | 424/473 |
| 2005/0095294 A1 * | 5/2005 | Parikh et al. | 424/470 |
| 2005/0214223 A1 * | 9/2005 | Bartholomaeus et al. | 424/10.1 |
| 2006/0246134 A1 | 11/2006 | Venkatesh | |
| 2007/0071819 A1 | 3/2007 | Kesarwani et al. | |
| 2007/0154547 A1 * | 7/2007 | Flanner et al. | 424/468 |
| 2008/0069878 A1 * | 3/2008 | Venkatesh et al. | 424/468 |
| 2009/0220611 A1 * | 9/2009 | Dargelas et al. | 424/495 |
| 2010/0179170 A1 | 7/2010 | Du Toit et al. | |
| 2010/0291191 A1 * | 11/2010 | Shoichet et al. | 424/450 |
| 2011/0217371 A1 | 9/2011 | Shin et al. | |
| 2012/0135050 A1 | 5/2012 | Dill | |

FOREIGN PATENT DOCUMENTS

EP   1 499 300 B1   3/2009

OTHER PUBLICATIONS

S.M.L. Abrams et al., "Pharmacodynamic and Pharmacokinetic Comparison of Two Formulations of Lorazepam and Placebo," Human Psychopharmacology, vol. 3, 133-138 (1988).
Paul Glue et al., "Pharmacokinetics of an Extended Release Formulation of Alprazolam (Xanax XR) in Healthy Normal Adolescent and Adult Volumteers," Am J. of Therapeutics 13, 418-422 (2006).
David J. Greenblatt et al., "Single- and Multiple-Dose Kinetics of Oral Lorazepam in Humans: the Predictability of Accumulation," J. Pharmacokinetics and Biopharmaceutics, vol. 7, No. 2, pp. 159-179 (1978).
David J. Greenblatt et al., "Comparative Single-Dose Kinetics and Dynamics of Lorazepam, Alprazolam, Prazepam, and Placebo," Clin. Pharmacology and Therapeutics, 44:326-334 (1988).
ATIVAN® (lorazepam) Tablets, Package Insert. BIOVAIL Pharmaceuticals, Inc. Mar. 2007.

* cited by examiner

*Primary Examiner* — Robert A Wax
*Assistant Examiner* — Olga V Tcherkasskaya
(74) *Attorney, Agent, or Firm* — Mark R. Buscher

(57) ABSTRACT

A pharmaceutical composition for delivering lorazepam in a prolonged fashion is achieved with prolonged release lorazepam pharmaceutical beads. The composition typically contains sustained release lorazepam beads and delayed sustained release lorazepam beads. The composition can provide once daily dosing that maintains 24 hour therapeutic effect under steady state conditions.

20 Claims, 3 Drawing Sheets

SUSTAINED RELEASE FORMULATIONS OF LORAZEPAM

The present application claims the benefit of priority under 35 U.S.C. §119(e) from prior U.S. provisional patent application No. 61/750,797, filed on Jan. 9, 2013 and from prior U.S. provisional patent application No. 61/762,833, filed on Feb. 8, 2013; the entire contents of each provisional application being incorporated herein by reference.

BACKGROUND OF THE INVENTION

The present invention relates to sustained release formulations of lorazepam and to methods of treating patients with a once-a-day dose of lorazepam.

Lorazepam is the generic name for the active pharmaceutical ingredient ±7-chloro-5-(2-chlorophenyl)-1,3-dihydro-3-hydroxy-2H-1,4-benzodiazepin-2-one, which has the following structure:

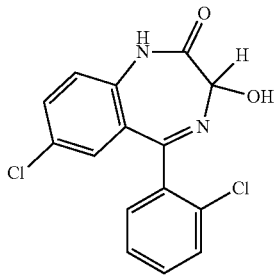 [SMILES: O=C1Nc2ccc(Cl)cc2C(c2ccccc2Cl)=NC1O]

Like other benzodiazepines, lorazepam has CNS activity and has proven to be a useful treatment for anxiety related disorders, such as: General Anxiety Disorder or Anxiety associated with Major Depression and others. It is almost insoluble in water. This compound was disclosed in U.S. Pat. No. 3,296,249.

Lorazepam has been sold commercially under the brand name ATIVAN® (originally by Wyeth, now by Valeant Intl) in the form of an oral immediate release tablet. The tablets contain 0.5 mg, 1 mg, or 2 mg of lorazepam and are usually administered two or three times a day (b.i.d and t.i.d, respectively) to achieve a total dose of 2 to 6 mg/day, though doses from 1 to 10 mg/day can also be used. According to the U.S. package insert material for ATIVAN®: "For anxiety, most patients require an initial dose of 2 to 3 mg/day given b.i.d. or t.i.d." The peak plasma concentrations (Cmax) typically occur about 2 hours (Tmax) after oral administration. Lorazepam has, according to the package insert, a half-life in human plasma of about 12 hours.

While the immediate release tablets of lorazepam, with a multi-dose per day regimen, have been available for several decades, thus far no once-a-day dosage form has been commercially introduced. Such a dosage form is often desirable. Besides the benefit of convenience, a sustained release version that could provide 24 hour therapeutic effect, but with lower peak plasma concentration levels than the immediate release tablet, may reduce side effects. For this reason, Abrams et al. investigated a sustained release tablet containing 2 mg of lorazepam and compared it to a 2 mg dose of lorazepam immediate release tablets (2×1 mg tablets). S. M. L. Abrams et al., "Pharmacodynamic and Pharmacokinetic Comparison of Two Formulations of Lorazepam and Placebo," *Human Psychopharmacology, Vol.* 3, 133-138 (1988). The sustained release tablet had, as expected, a longer Tmax (median 8 hours) and a lower Cmax (12 ng/ml) than the immediate release tablets (2 hours and 22 ng/ml, respectively). But the relative bioavailability was reduced in the sustained release tablet such that after 30 hours the AUC was only about 85% of the AUC achieved with the immediate release tablets. Abrams et al. also noted that "the [serum] concentrations of both formulations were similar between 10 and 30 h[ours]." Thus, despite providing some delay in the rise of lorazepam serum concentrations and a lower Cmax, the sustained release tablet apparently did not serve to extend the therapeutic duration of lorazepam beyond that achieved with immediate release tablets.

The long half-life of lorazepam in blood plasma makes it a classically disregarded candidate for the development of a once daily formulation. Also, a drug product that provides 24 hour therapy from two doses per day, as opposed to three or more doses per day, is generally considered to have achieved the majority of patient compliance benefits. If a single daily dose formulation was desired, an immediate release lorazepam tablet could be used to provide a complete daily dose because of the long half-life of lorazepam in blood plasma. But administering a complete daily dose in a single immediate release dosage form would increase the Cmax and the peak-trough variations (concentration differences between Cmax and Cmin) beyond those attained in conventional b.i.d. administration (i.e., twice-daily dosing), and thus would likely increase the risk of drug related adverse events, i.e., side effects. Using a sustained release formulation can reduce the rate of increase in plasma drug concentration and the value of Cmax, but runs the risk of sub-therapeutic plasma concentration levels, especially near the end of the dosing cycle, and/or lower overall drug exposure than the current b.i.d. immediate release tablet regimen.

A lorazepam formulation that provides a sustained release profile with the potential for an effective and well tolerated once daily dosing regimen would be advantageous.

SUMMARY OF THE INVENTION

The present invention relates to sustained release lorazepam compositions that provide rather prolonged release of lorazepam. A first aspect of the invention relates to a pharmaceutical composition, comprising (i) lorazepam sustained release beads and (ii) lorazepam delayed sustained release beads, wherein the total amount of lorazepam contained in said composition is 0.5 to 10 mg. The delayed sustained release beads, as explained in more detail below, are sustained release beads having a coating that delays the start of the sustained release. Preferred embodiments permit once daily administration of the composition with 24 hours of therapeutic effect. Typically the preferred composition is a capsule containing the two types of beads, but is not limited to such.

Another aspect of the invention relates to a sustained release lorazepam pharmaceutical composition, which comprises lorazepam prolonged release beads in sufficient amount and duration that in a single dose pharmacokinetic study, said composition has a pharmacokinetic profile that comprises a Tmax at 4 hours or longer and continued absorption of lorazepam beyond 20 hours, preferably for at least 24 hours, more preferably for at least 28 hours, and still more preferably for at least 30 hours; said composition being an oral dosage form containing 0.5 to 10 mg of lorazepam. The composition when administered once daily to a patient, maintains a therapeutic effect for at least 24 hours By providing a prolonged release dosage form that achieves prolonged absorption, lorazepam can accumulate in the blood plasma and provide favorable steady state pharmacokinetic profiles.

A further aspect of the invention relates to a method of treating a lorazepam-treatable condition in a patient, which comprises administering once a day to a patient in need thereof one of the above-mentioned pharmaceutical compositions in a sufficient dose to provide 24 hour therapeutic effect during steady state conditions. The composition may comprise (i) lorazepam sustained release beads and (ii) lorazepam delayed sustained release beads, wherein the total amount of lorazepam contained in said composition is 0.5 to 10 mg. Typical lorazepam-treatable conditions include anxiety disorders such as Generalized Anxiety Disorder and anxiety associated with major depression, but is not limited thereto.

DETAILED DESCRIPTION OF THE INVENTION

Figure 1:
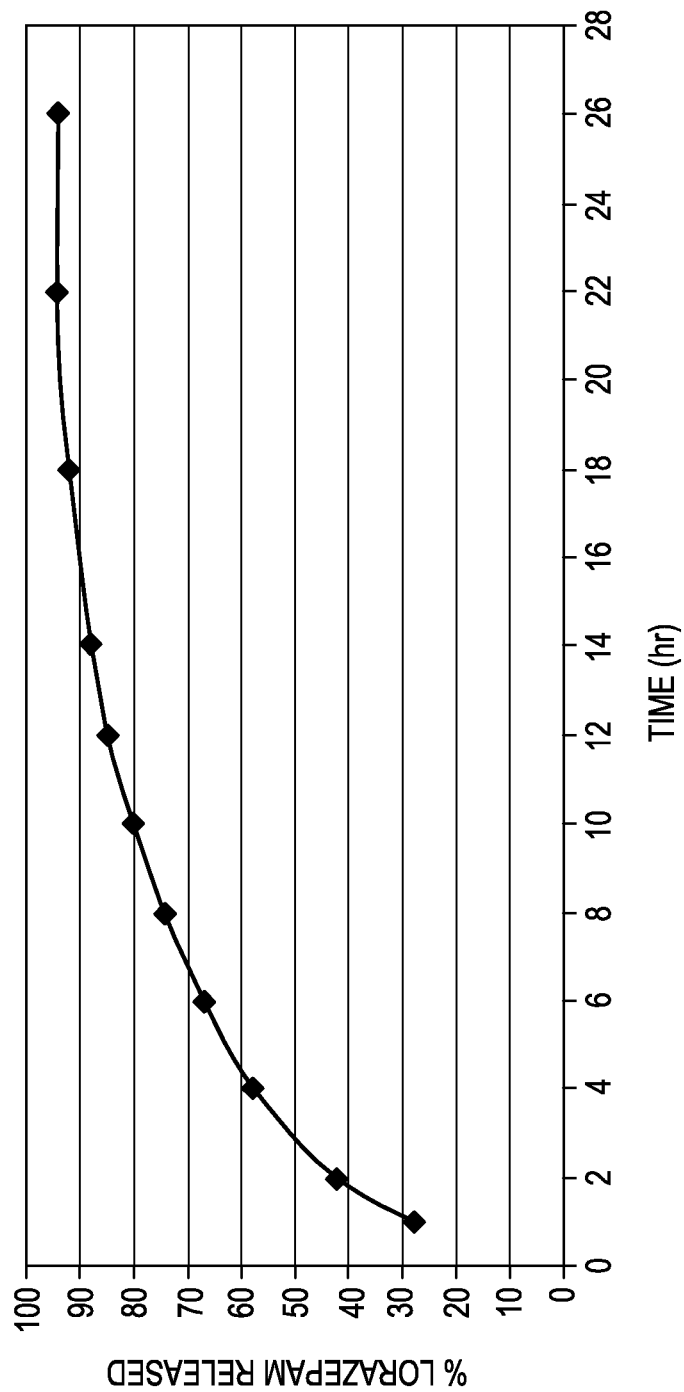
FIG. 1 represents the dissolution of the lorazepam sustained release beads made in Example 1 in a two media dissolution test.

The present invention relates to the discovery that sustained release formulations of lorazepam that have a rather prolonged release or absorption characteristic(s) can provide advantageous steady state pharmacokinetic profiles including an effective once-a-day dosing regimen. Surprisingly, by continuing to provide even small amounts of lorazepam late in the dosing cycle, the accumulation of lorazepam in the blood can be sufficiently bolstered and lead to beneficial steady state pharmacokinetic profiles. In this way, the goal of lower Cmax, lower peak-trough variation, but proper drug exposure and limited risk of sub-therapeutic blood levels can be achieved.

One aspect of achieving the prolonged release/absorption of lorazepam relates to lorazepam formulations comprising two types of sustained release lorazepam beads. The first type begins releasing shortly after ingestion and continues releasing for a prolonged period of time. The second type has a delay owing to a coating that will delay the onset of release from the bead. Once the coating is sufficiently removed and/or permeable, the delayed sustained release bead begins to release the drug for a prolonged period of time. By controlling the rate of sustained release in each type of bead, controlling the delay via the coating, and combining them into a unit dosage form, such as a capsule, it is possible to provide a once-a-day dosing administration routine with 24 hour therapeutic effect. In preferred embodiments, the unit dosage form containing the two kinds of beads can have similar or improved efficacy and/or reduced side effects in comparison to the same total dose of conventional immediate release tablets that are given at least twice daily or b.i.d. For clarity, dosing regimens, such as once daily, twice daily or b.i.d., etc., are intended to refer to equal time spaces between successive doses. For example, a b.i.d. regimen would mean the dose is administered every 12 hours; a once-a-day dosing regimen would mean dosing once every 24 hours; etc.

The lorazepam sustained release beads can be any kind of pharmaceutical bead, pellet, or other pharmaceutical particulate that contains lorazepam and releases the lorazepam in an extended manner. This sustained or extended release characteristic is in contrast to an immediate release profile which generally requires release of 90% of the lorazepam in 30 minutes as measured in a suitable in vitro dissolution test. For purposes of the present invention, a sustained release lorazepam bead does not release 90% of the lorazepam in less than 2 hours in a USP Type I apparatus (Basket) using 0.1 N HCl as the dissolution media.

The sustained release lorazepam beads preferably release 20 to 80%, typically 20 to 70%, more typically 25 to 60%, and often 30 to 50%, of the lorazepam in 2 hours. Further, the release profile of these preferred beads often includes achieving 90% after 4 hours (i.e., beyond the 4 hour point of the dissolution test), more typically after 6 hours, and in some embodiments after 8 hours. Indeed, in some rare embodiments, 90% release may not actually be achieved in the dissolution test; e.g., the maximum release in dissolution testing may only be 85%, for example. Such a result would mean that 90% release would not have occurred or been achieved before 8 hours as per an embodiment of the invention. The point is that 90% is not released before the specified time point, regardless of whether 90% release was eventually achieved or not. Some preferred sustained release lorazepam beads are so prolonged that they do not release 90% of the lorazepam before 10 hours, more preferably before 12 hours, and in some embodiments before 13 or even 14 hours. In most embodiments, however, 90% release is ultimately achieved and usually occurs before 20 hours, generally by 18 hours and often by or around 16 hours. In some embodiments, the 90% release occurs before 15 hours or even before 14 hours, such as by 12 or 13 hours. Because the release curve may be relatively flat near the end of the release, small changes in the percent amount of released drug may take hours to occur. Accordingly, a broad time window for achieving 90% release may nonetheless include relatively similar release curves. Typical time frames for achieving 90% release include 8 to 22 hours such as 8 to 20 hours or 8 to 18 hours, more typically 10 to 18 hours, and sometimes 12 to 16 hours. Often the dissolution profile will include achieving 80% release within the range of 6 to 16 hours, typically 6 to 14 hours, more typically 6 to 12 hours, and sometimes 7 to 12 hours. In some embodiments, 50% of the lorazepam is released within 1 to 5 hours and 70% is released within 4 to 10 hours. While each of the above release amount-time relationships can be applied individually, preferred sustained release lorazepam beads of the invention meet any combination of two or more of the above relationships; e.g., the release curve meets (i) the 20-70% at 2 hours relationship, (ii) the 70% within 4 to 10 hours relationship, and (iii) the 90% within 10 to 19 hours relationship. Unlike the definition of a sustained release lorazepam bead, each of the above-described preferred release relationships for sustained release lorazepam beads is determined/measured using a two media in vitro dissolution test using a USP Type I apparatus (Basket).

In the "two media dissolution test," the first two hours are carried out using a media that comprises 0.1 N HCl. At 2 hours the media is changed to a media that comprises a phosphate buffer and has a pH of 7.4. As is understood in the art, the first media approximates the stomach conditions while the second media approximates the intestinal conditions. Other ingredients can be present in the media, such as enzymes, etc., as is known in the art, e.g., in formulating simulated intestinal fluid (SIF). The two media dissolution test is conducted at 37° C. and can use 500 ml or 900 ml vessels. The stirring speed is typically 100 rpm, though the speed can be adjusted, such as to 75 or 50 rpm, etc., if necessary for the dissolution testing to give more useful information for a particular embodiment. For clarity, when options are provided such as different size vessels, a bead that meets the profile release data under any option is considered to meet the release criteria; e.g., a bead that exhibits at 2 hours 31% release in a 900 ml vessel but only 27% release in a 500 ml vessel is considered to meet the range of 30 to 50% release at 2 hours because it met the range in one of the options. The percentage of lorazepam released is based on the nominal or label amount (e.g., 2 mg), as is conventional in the art, and not on the actual assayed amount (e.g. 1.96 mg). In a well-controlled process, the actual assayed amount is generally within +/−5% of the label amount. The percentage of release at a point in time refers to the cumulative release up to that point in time, as per the conventional usage of these terms in the art. The amount of lorazepam released from the beads (i.e., dissolved into the dissolution media), can be determined by ordinary methods using routine skill.

The delayed sustained release lorazepam bead comprises a sustained release lorazepam bead, such as those having the preferred in vitro dissolution release profile described above, having an outer coating layer that causes a delay in the start of the release. Generally the delay coating is designed to achieve a release delay in vivo of at least 3 hours, often within the range of 4-8 hours, before significant release starts. Delay coatings are generally known in the art and are usually based on pH, solubility, or a combination. A pH-dependent coating, also known as an enteric coating, changes solubility based on pH. At low pH such as found in the stomach, the coating is insoluble and prevents the body fluids from reaching and releasing the drug from the beads. At higher pH such as found in the intestines, the coating becomes soluble and is removed and/or becomes permeable thereby permitting the body fluids to reach and release the drug from the beads. The delay is controlled by the pH at which the coating becomes soluble and by the coating thickness/amount. A solubility-based coating uses a low water-soluble coating that slowly dissolves or erodes to reveal the underlying bead and thereby permit drug release to start. The solubility and thickness/amount of the coating control the time of the delay (e.g., how long until the coating is gone). Both kinds of coating can be used together in a hybrid fashion.

Though delay coatings of various constructions can achieve the same effect in vivo, they may provide different results in an in vitro dissolution test, depending upon the conditions, because of their design principles. For example, using the two media in vitro dissolution test described above, a pH-dependent delay coating will start to permit drug release shortly after the changeover to the pH 7.4 media. A solubility-based delay coating that is not pH-dependent will not be as affected by the media changeover.

Using the two media in vitro dissolution test as described above, a pH-dependent delay coating should exhibit essentially no lorazepam release, i.e., less than 3%, typically less than 1%, and generally less than or near the limit of detection, in the first media (e.g. for the first 2 hours). In practice, sometimes slightly higher amounts of lorazepam are released during the first two hours; generally not more than 10%, usually not more than 5%. The delayed sustained release beads have appreciable release starting in the second media. Preferred embodiments achieve 20 to 80%, often 25 to 50%, release of the lorazepam in 4 hours and optionally further achieve 90% release after 6 hours, more typically after 8 hours, and in some embodiments after 10 hours. In some embodiments, 50% of the lorazepam is released within 4 to 8 hours and 70% is released within 7 to 12 hours. Indeed, the preferred release relationships described for the sustained release beads can also describe the release from delayed sustained release beads with the addition of 2 hours onto the time to account for the delay in release during the initial 2 hours in 0.1N HCl. For example, the delayed release lorazepam bead embodiment where 90% release is not achieved before 10 hours is translated to the delayed sustained release bead as not releasing 90% before 12 hours, e.g., 2 hours later in the dissolution test.

For delay coatings that are solubility-based, pH-independent, the release profile using the two media in vitro dissolution test generally includes achieving 10% release not earlier than 2 hours and more typically not earlier than 4 hours and often at 6 hours or later. In some embodiments, these delayed sustained release lorazepam beads achieve 20 to 80% release, and often 25-50% release, of lorazepam in 8 hours. Achieving 90% release of lorazepam often occurs after 10 hours, more typically after 12 hours but before 24 hours. For clarity, a delay coating that has both pH-dependent polymers and pH-independent polymers is considered to be a pH-dependent delay coating.

The pharmaceutical composition containing the two kinds of beads is typically a unit dosage form for oral administration. The beads are frequently filled into a capsule but can also be mixed with excipients and compressed into tablets. If desired, the tablets could be bi-layer tablets having the sustained release lorazepam beads in one layer and the delayed sustained release lorazepam beads in the other layer, but such is not required. Other compositions including sachets containing the beads are also possible. The sachet composition, which may additionally include excipients such as a sweetener or taste masking agent, etc., can be swallowed directly from the package or it can be sprinkled onto food or deposited into a drink such as water or juice and then immediately consumed with the food or drink, respectively. Usually the composition contains only the two populations of beads: the sustained release lorazepam beads and the delayed sustained release lorazepam beads. It is possible, however, that additional lorazepam bead types or populations are contained. Immediate release lorazepam beads may additionally be included, for example. The presence of immediate release lorazepam is generally disfavored and, if present, preferably accounts for 20% or less, more preferably 10% or less, of the total amount of lorazepam in the composition. Typically the amount of immediate release lorazepam is essentially zero, meaning zero and trivial amounts not intended to provide therapeutic effect or modulation of the steady state blood plasma concentration and generally less than 3%, less than 2%, and less than 1%. In general, when additional lorazepam beads are present, at least 80%, sometimes at least 90%, and in some embodiments at least 95%, of the total amount of lorazepam is contained in the combination of the sustained release lorazepam beads and the delayed sustained release lorazepam beads. As stated above, the combination of sustained release lorazepam beads and the delayed sustained release lorazepam beads typically provide 100% of the lorazepam content in the composition of the invention. In all embodiments, the ratio of sustained release lorazepam beads to delayed sustained release lorazepam beads is not particularly limited and is generally from 1:0.5 to 1:4, respectively, based on the amount of lorazepam. Often the ratio is 1:1+/−30%, more typically +/−25%, and sometimes +/−10%. Typically, though not necessarily, lorazepam is the only active in the composition.

The pharmaceutical composition contains 0.5 to 10 mg of lorazepam. Lorazepam and its synthesis are well known and the drug is generally commercially available. Lorazepam can be amorphous or crystalline. Though it has a diazepine ring nitrogen that could be used for forming a salt, typically lorazepam is used as a non-salt or free base. Lorazepam is usually presented as a racemic mixture, but an individual isomer or non-racemic mixtures could also be used. For purposes of the present invention, "lorazepam" is intended to embrace all such pharmaceutical forms of lorazepam including pharmaceutically acceptable salts, racemic and non-racemic forms or individual isomers, crystalline forms thereof including hydrates and solvates, and amorphous forms, unless noted otherwise. Typical amounts for commercial reasons are often from 1 to 6 mg, especially 1 to 4 mg, including 1 mg, 2 mg, 2.5 mg, 3 mg, and 4 mg; though each integer from 1 to 10, inclusive, also represents suitable specific dose amounts. In some embodiments, the amount of lorazepam in milligrams is an integer from 1 to 10 plus (or minus) 0.25 or 0.5 mg. The extra 0.25 or 0.5 can be split evenly between the sustained release lorazepam beads and the delayed sustained release lorazepam beads. Alternatively the entirety of the extra amount can be in the sustained release lorazepam beads or entirely in the delayed sustained release lorazepam beads, or any variations in between. For example, in formulating a total lorazepam dose of 2.25 mg, 1 mg may be present as sustained release lorazepam beads and 1.25 mg may be present as delayed sustained release lorazepam beads (e.g., the extra amount is entirely in the delayed sustained release lorazepam beads).

Sustained release lorazepam beads can be formulated using any sustained release bead technique, including matrix-based beads or barrier coating-based beads, in order to achieve the desired in vitro dissolution release profile. Matrix-based beads are generally made by granulating and extruding a mixture comprising the polymer matrix material(s), the lorazepam and optionally additional excipients such as binders and fillers. Typical polymer matrix materials include, but are not limited to, various grades of hydroxypropyl methylcellulose (HPMC), polyacrylates such as various Eudragit brand compositions, and polyethylene oxides. Binders and fillers include starch, microcrystalline cellulose (MCC), etc. The extruded beads are typically subject to spheronization and drying. Barrier coating-based beads typically start with a nonpareil seed core, such as a sugar core or MCC core, upon which successive functional coating layers are formed. For instance, a core could be coated with a sealing coat, followed by a drug layer coat having the drug and a binder, followed by a release-controlling polymer coat layer (the barrier layer). The barrier layer is generally, but not limited to, a water insoluble polymer as a film forming material. Examples include celluloses such as ethyl cellulose, and acrylate polymers and copolymers. Additional materials are usually included to enhance performance of the film. These include but are not limited to: plasticizer(s) to confer flexibility and ensure that coat cracking or physical changes do not compromise the drug releasing properties; antitacking aids to minimize particle adherence/aggregation during processing or storage; dispersants/wetting agents to aid in surface coating; and pore formers where indicated to provide channels for drug release. In either kind of sustained release bead, the lorazepam drug content is generally low and typically less than 7%, more typically less than 5%, and often 1-4% by weight, based on the weight of the bead. The sustained release lorazepam beads typically have a size of less than 1 millimeter, and frequently the beads are within the size range of 0.4-0.8 millimeters.

The delayed sustained release lorazepam beads are a sustained release lorazepam bead core having a delay coating layer. The sustained release lorazepam bead used as the core can be the same as, or different from, the sustained release lorazepam beads used in the first population. In the typical embodiment, the delay coating is the well known enteric coating; that is, one based on polymers having pH-dependent solubility. These polymers are insoluble or substantially insoluble in an acidic aqueous media but become more soluble as the pH increases. Generally such polymers have free acid groups such as cellulose acetate phthalate or polymethacrylates and their copolymers, but is not limited to such. A useful enteric coating can be based on Eudragit FS 30 D. Other possible enteric coating materials include Eudragit S 100 and Eudragit S 12.5. Enteric coatings can be based on a single enteric polymer or a combination and typically further contain a plasticizer. The beads can be coated by conventional means often via a liquid media which is removed upon drying to leave the polymer-based coating. The delayed sustained release lorazepam beads are usually a little larger than the sustained release lorazepam beads owing to the coating thickness. Nonetheless, the delayed sustained release lorazepam beads are also typically not greater than 1 millimeter and often within the range of 0.4 to 0.9.

The enteric coating can prevent release of the drug in the stomach and/or intestine until the enteric coating is sufficiently soluble to permit diffusion, erosion, and/or is dissolved away. By selecting the kind of polymer(s) and the amount of coating, the enteric coating can provide any desired level of pH protection; e.g. release/soluble at pH 6, 6.8, 7, etc. Generally, the present invention prefers an enteric coating that is designed to release at pH 7 or greater, especially about pH 7.4. Commercially available enteric coatings are often designated by the manufacturer as having a release a specified pH. Those designated as having a release at pH 7 are thus deemed to be designed to release at pH 7 and are sometimes described as providing colon release. In the GI tract, the pH gradually increases in the small intestine from pH 6 to about pH 7.4 in the terminal ileum. In preferred embodiments of the present invention, the delayed sustained release lorazepam beads are targeted to begin releasing in or near the terminal ileum. Even if designed to release at pH 7.4, for instance, enteric coatings are generally not perfect and often begin permitting appreciable release of the drug before pH 7. For purposes of the present invention, an enteric coating "designed to release at pH 7 or higher" includes those that have a significant reduction in release during hours 2-6 when the two media dissolution test is modified by replacing the pH 7.4 phosphate buffer media with pH 6.8 phosphate buffer media. A significant reduction is at least 50%. For example, if the delayed sustained release bead released 30% of the lorazepam at hour 4 (second hour in the pH 7.4 buffer media), the same bead would only release 15% or less at hour 4 when tested using the lower pH 6.8 buffer media. This 50% reduction would also apply at hour 6. Often the reduction is more significant, achieving only 35% or less, sometimes only 25% or less, of the release in pH 7.4 buffer when tested using the pH 6.8 buffer. As shown in the Examples below, Eudragit FS 30 D is suitable for providing an enteric coating "designed to release at pH 7 or higher."

Some embodiments of the delayed sustained release lorazepam beads have a release mechanism and enteric coating sufficient to provide 20-50% release of lorazepam at 4 hours and 50-80% release at 8 hours in the two media dissolution test; but less than 10% release of lorazepam at 4 hours and less than 35%, preferably less than 30%, release in 8 hours in the modified two media dissolution test using pH 6.8 buffer media instead of pH 7.4 buffer media.

Alternatively, the delay coating can be a time delay coating based on thickness and water solubility rather than sensitivity to pH. Generally, film formers for time-delayed release can be water soluble, dissolving during GI transit, or water insoluble which swell under physiological conditions whereupon drug release is controlled by diffusion through the swollen coating. The duration of time delay is influenced by the hydrophilic and swelling properties of the polymer and coat thickness. Examples of such polymers are cellulose acetates, ethylcellulose, glycerides, substituted methacrylates, polyvinyl acetate, HPMC, and carboxymethylcelluloses (CMC). In some embodiments the coating contains polymers having low water solubility which slowly dissolve away. In other embodiments, the coating contains a mixture of water soluble and water insoluble polymers (or higher and lower water soluble polymers). By controlling the ratios of the polymers and the thickness/amount, the desired time delay can be achieved. Examples of water soluble polymers include cellulose ethers such as HPMC, methylcellulose, hydroxyethylcellulose, Na CMC, and polyvinylpyrrolidone (PVP). Less soluble or insoluble polymers include ethylcellulose and polymethacrylates.

In practice, the pharmaceutical composition of the invention can permit a once daily dosing regimen. Controlling the amount of lorazepam provided as (i) sustained release lorazepam beads and as (2) delayed sustained release lorazepam beads, as well as the degree of sustained release and delay provided, can produce useful blood plasma concentration levels of lorazepam in a patient. The sustained release lorazepam beads release the lorazepam over several hours shortly after administration. The delayed sustained release lorazepam beads begin the sustained release after an initial delay, typically of several hours. In some embodiments, the delay is around 6 hours (e.g., 5-7 hours, usually 5-6 hours) and/or begins in the high pH of the terminal ileum. Average transit time to the terminal ileum is generally considered to be approximately 6 hours. Thus the full day's dose of lorazepam can be spread out over time to reduce blood plasma fluctuations while assuring the minimum therapeutic concentrations are maintained. In this way, preferred compositions of the invention can provide therapeutic effect for 24 hours under steady state conditions with once daily dosing. Quantitatively, certain preferred embodiments of the invention will provide a blood plasma concentration of 10 ng/ml or more for at least 20 hours, often at least 22 hours, and sometimes for 24 hours under steady state conditions over a 24 hour period (e.g., from daily-dose to daily-dose).

For clarity, the term "steady state" is used in its ordinary sense in the pharmaceutical arts. It does not mean constant, but rather the dynamic equilibrium that is obtained after consistent successive administrations of a drug, typically several days (e.g., 5 times the ½ life, or 3-5 days in the case of lorazepam). For example, a patient already taking lorazepam immediate release tablets on a regular schedule (two or three times per day) has lorazepam in his/her blood when the next dose is administered. After ingestion, the dose is released and the amount of lorazepam in the blood increases to a maximum blood plasma concentration or "Cmax." The lorazepam is concurrently being metabolized and/or removed from the blood by biological actions of the body and so the blood plasma concentration falls. The decline in drug blood plasma concentration will continue until the next dose of lorazepam is taken. The drug blood plasma concentration will reach its lowest concentration level, the "Cmin," just before the new dose of lorazepam is absorbed into the blood. The new dose causes a rise in blood plasma concentration and the cycle repeats, reaching the Cmax once again followed by a fall to the Cmin and a new administration of lorazepam, etc. In contrast to the steady state, the first dose of lorazepam produces different blood plasma values because no lorazepam is in the blood at the time of the dose. The Cmin for such a single dose experiment is zero at the outset. The Cmax is typically noticeably lower than the steady state Cmax. Because the present invention is applicable for chronic administration of lorazepam (one or more weeks and perhaps months or years), the steady state parameters can be more meaningful. Indeed, in some embodiments of the present invention, a single dose study (e.g., initial dose) will not provide a therapeutic concentration in the blood stream sooner than 1 hour, often not before 2 hours, and in some embodiments not before 3 hours. In some embodiments, a minimum therapeutic blood plasma concentration can be taken to be 10 ng/ml.

Preferred embodiments provide a lorazepam blood plasma steady state Cmax from daily dosing that is about equal to, or less than, the steady state Cmax obtained from dosing the same total daily amount of lorazepam via immediate release tablets through b.i.d or t.i.d. regimens. The term "about equal" means that the steady state Cmax of the controlled release composition is within +/−35%, preferably with +/−20% of the steady state Cmax for the corresponding immediate release tablets given b.i.d. or t.i.d (having the same total daily dose). In some embodiments, the steady state Cmax of the controlled release composition approximates, or is less than, the steady state Cmax for the corresponding immediate release tablets given b.i.d. The term "approximates" means +/−15%, preferably +/−10%. The lorazepam blood plasma steady state Cmin for the sustained release composition is preferably about equal to, or greater than, the steady state Cmin for the corresponding immediate release tablets given b.i.d. (having the same total daily dose). In some embodiments the steady state Cmin approximates or is greater than the Cmin for the corresponding immediate release tablets given b.i.d. The terms "about equal" and "approximates" have the same meaning as regards the Cmax.

Though the lorazepam steady state Cmax and Cmin values of the inventive composition may be about equal to the Cmax and Cmin of the corresponding dose of immediate release tablets in b.i.d., the composition is believed to lower the risk of adverse events, such as sedation, somnolence, dizziness, memory impairment, etc. Beyond Cmax, the rate of increase of lorazepam blood concentration is also believed to correlate with adverse event risk: a slower rise in lorazepam blood plasma concentration has less risk of adverse events. The composition of the present invention in a once daily dose form provides a slower increase in lorazepam blood concentration than the use of immediate release tablets. This difference can be expressed by the "Tmax," i.e., the time to regain steady state Cmax after a dose is administered. Preferred embodiments of the pharmaceutical composition of the invention typically provide a Tmax not sooner than 4 hours, often not sooner than 6 hours, more typically not sooner than 7 hours, and often not sooner than 8 hours.

The use of two sustained release bead populations, one further having a delay before release starts, can provide for advantageous pharmacokinetic profiles. The release of drug can be effectively smoothed and prolonged leading to relatively flat plasma concentration vs. time curves around the Cmax (e.g. flat tops). Often the curve will be constant within +/−2 ng/ml variation for at least 8 hours, preferably for at least 10 hours, and sometimes at least 12 hours.

Another aspect of the present invention relates to a sustained release lorazepam pharmaceutical composition, which comprises lorazepam prolonged release beads in sufficient amount and duration that in a single dose pharmacokinetic study, the composition has a pharmacokinetic profile that comprises a Tmax at 4 hours or later and continued absorption of lorazepam beyond 20 hours, preferably for at least 24 hours, more preferably for at least 28 hours, and still more preferably for at least 30 hours. The composition is an oral dosage form, such as a capsule filled with beads, containing 0.5 to 10 mg of lorazepam. Typically the composition maintains a therapeutic effect for 24 hours (in steady state) when administered in a once daily dosing regimen.

The "prolonged release beads" are any pharmaceutical particulates that provide long term sustained release, optionally with an initial delay. The prolonged release beads can be used as the sole bead in the composition or in combination with one or more other beads including immediate and/or sustained release beads. The prolonged release beads can be, for example, a slow sustained release bead optionally used in conjunction with immediate release and/or relatively quick sustained release beads. Or the prolonged release bead can be a hybrid bead having two releases of lorazepam; i.e., a first release from an outer coating followed by a sustained release from a more interior portion of the bead. The hybrid bead can be used alone or in combination with immediate and or sustained release beads. The prolonged release beads can also be the delayed sustained release beads as described above and used in conjunction with sustained release beads and optionally with immediate release beads.

The prolonged release beads are present in the sustained release composition in a sufficient amount and with a sufficiently prolonged release (duration) that absorption of lorazepam is detectable even after 20 hours of a pharmacokinetic study. The study is conducted with fasting during the administration and runs for 120 hours. The continued release of lorazepam from the dosage form and concomitant absorption can be deduced by comparing the loss of concentration of lorazepam in the blood plasma to the known (or measured) elimination rate of lorazepam. As long as any appreciable amount of lorazepam is being absorbed into the body, the decline in blood plasma concentration will be slower than the fundamental lorazepam elimination rate. A comparison to the concentration decline of an immediate release tablet can be used to confirm or determine whether a sustained release composition has a slower decline and thus is achieving release and absorption of the lorazepam. Graphically the difference is more readily appreciated when plotted using a log scale for concentration. The "continued absorption" refers to the relatively uninterrupted release and absorption of lorazepam provided by a sustained release composition. The absorption may have an initial delay, but once release and absorption begin, a sustained release composition will continue to release lorazepam until the drug loaded dosage form is essentially exhausted. In contrast, a non-sustained release composition such as a composition that provides two bolus doses of lorazepam, would not have "continued absorption" even if the second bolus was released at hour 22.

By providing a sufficient amount of lorazepam in the form of the prolonged release beads and for a sufficient duration that release of lorazepam and its absorption can be seen beyond 20 hours of the single dose pharmacokinetic study, the steady state Cmin (as well as the Cmax) can be surprisingly improved. Preferably the absorption is ongoing to at least 24 hours, more preferably at least 28 hours, still more preferably at least 30 hours, and even at least 32 hours. While the absorption is most likely slight as determined from a single dose pharmacokinetic study, its cumulative effect can provide a significant increase in Cmin, Cmax, and total absorption/exposure, i.e., Area Under the Curve (AUC). Because of the prolonged release and absorption, in some embodiments, around half of the total AUC from 0-120 hours is achieved in the first 24 hours of a single dose pharmacokinetic study; generally from 40-60%, often 45 to 55%, of the total AUC in 0-120 hours is achieved in hours 0-24. Part of the ability to provide drug for absorption for so long is attributable to the bead or particulate form of the lorazepam. Generally the transit time through the GI tract is 12 to 24 hours. But for beads having a particle size of 1 mm or less, the transit time can be much longer. The beads may percolate up and down the intestinal tract and/or may get delayed in lumen tissue clefts, etc. Thus, when the next administration of the sustained release composition occurs, the prior dose may still be releasing lorazepam. The previously described composition having lorazepam sustained release beads and lorazepam delayed sustained release beads preferably meets one or more of these prolonged absorption and AUC goals, wherein the delayed sustained release beads serve as the prolonged release beads. Likewise, the sustained release lorazepam pharmaceutical composition, which comprises lorazepam prolonged release beads, typically meets the Cmin, Cmax, and Tmax values, including preferred values, as previously described for the composition having lorazepam sustained release beads and lorazepam delayed sustained release beads.

A specific embodiment of the present invention relates to a pharmaceutical composition that contains 2 mg of lorazepam, split about evenly between sustained release and delayed sustained release lorazepam beads, and provides for once daily dosing. Such a composition preferably provides a steady state Cmax of 26 ng/ml or less, usually 23 ng/ml or less when administered once daily. The Cmin, however, does not fall below therapeutic levels. Preferably the Cmin is at least 10 ng/ml, sometimes at least 11 ng/ml, and can be at least 12 ng/ml, when administered once daily. The Tmax is typically within the range of 4 to 12 hours after once daily administration.

Typically the compositions of the present invention exhibits dose proportionality within the range of 1-6 mg of lorazepam. The proportionality is typically with respect to the AUC (total exposure) but is also preferably found with the steady state Cmax and/or Cmin. The following approximation can apply to preferred embodiments regarding the steady state Cmax. Each 1 mg of lorazepam provides a lorazepam blood plasma steady state Cmax of not greater than 10 ng/ml +20%. Thus under this embodiment, a 2 mg dose preferably provides a steady state Cmax within the range of 20-24 ng/ml or less, preferably 20-24 ng/ml; a 3 mg dose preferably provides a steady state Cmax within the range of 30-36 ng/ml or less, preferably 30-36 ng/ml, etc. These values assume once daily dosing. The lorazepam steady state Cmin is preferably at least 5 ng/ml for each 1 mg of lorazepam. For example, 2 mg of lorazepam preferably has a lorazepam blood plasma steady state Cmin of at least 10 ng/ml; while 4 mg of lorazepam preferably has a lorazepam blood plasma steady state Cmin of at least 20 ng/ml; etc. Again these values assume a once daily dosing regimen.

For clarity, all of the values for steady state Cmax, Cmin, and Tmax can be for a single subject but more commonly are an average of multiple subjects, e.g., multiple patients, multiple participants in a bioavailability study, etc. Also, the steady state values can be calculated from a single dose pharmacokinetic study by methods known in the art. Such calculated values (also called "simulations") are also suitable for determining the steady state values for purposes of the present invention.

The pharmaceutical compositions of the invention can be used to treat any lorazepam-treatable condition. These conditions are most often related to the treatment or management of anxiety related disorders. Examples include, but are not limited to: Generalized Anxiety Disorder and anxiety associated with major depression. But other uses for lorazepam can also apply to this invention; e.g., PTSD, insomnia and/or sleep disorders, bipolar disorder, obsessive-compulsive disorder (OCD), social anxiety disorder, convulsions, etc. The pharmaceutical compositions of the present invention are generally administered once per day. Though the dose is usually administered once daily, some clinicians may elect to divide the total daily dose amount for some patients into one or more administrations per day.

The invention will be further described with respect to the following non-limiting example.

Example 1

Sustained Release Lorazepam Beads were Made Having the Following Nominal Composition

| Component | Reference to Quality Standards | Function | Unit Composition | |
|---|---|---|---|---|
| | | | mg/Unit[a] | % w/w |
| Lorazepam | USP | Active ingredient | 2.00 | 3.0 |
| Hypromellose K100 premium LV | USP | Release control agent | 0.67 | 1.0 |
| Starch pregelatinized | NF | Binder | 6.67 | 10.0 |
| Microcrystalline cellulose special | NF | Filler | 57.33 | 86.0 |
| Purified water | | | —[b] | |
| Total | | | 66.67 | 100.0 |

[a] = Equivalent weight of core beads to obtain a 2 mg dose of Lorazepam.
[b] = Removed during processing.
USP = United States Pharmacopeia;
NF = National Formulary The beads were made by screening (30 mesh) the lorazepam, HPMC, and starch and mixing for 5 minute increments. The MCC was screened (30 mesh) and subsequently added with 10 minutes of mixing. The dry mixture was granulated with the addition of water, extruded, and spheronized. The beads were dried to a residual moisture content of less than 3% w/w and fraction screened between 40 mesh and 25 mesh. Samples of the beads were subjected to a two media in vitro dissolution test and the results are shown below. The average is also graphically shown in FIG. 1.

Example 2

Delayed sustained release lorazepam beads were made by using the above sustained release lorazepam beads and applying an enteric coating. The enteric coating was designed to release at pH 7 or higher and specifically was intended to permit free release at pH 7.4. The resulting delayed sustained release lorazepam beads have the following nominal composition.

| Component | Reference to Quality Standards | Function | Unit Composition | |
|---|---|---|---|---|
| | | | mg/Unit[a] | % w/w |
| Example 1 beads (core) | USP | Active ingredient | 66.7 | 82.11 |
| Eudragit FS 30D | | Delayed release control agent | 12.1 | 14.92 |
| PlasACRYL T20 | | Plasticizer | 1.21 | 1.49 |
| Colloidal silicon dioxide (optional) | USP | Anti-tacking agent | 1.20 | 1.48 |
| Purified water | | | —[b] | |
| Total | | | 81.21 | 100.0 |

[a] = Equivalent weight of coated beads to obtain a 2 mg dose of Lorazepam. Coating level is for a 20% weight gain.
[b] = Removed during processing.
USP = United States Pharmacopeia.

The delayed sustained release lorazepam beads were made by coating the beads obtained according to example 1. The Eudragit, plasticizer, and water were mixed and screened (35 mesh) to form a coating solution/suspension. The core beads were coated with the coating solution/suspension using a Glatt fluid bed drier. The optional colloidal silicon dioxide can be further coated via a spray drier. The coated beads are then dried and oversized beads are removed by using an 18 mesh screen cutoff.

Figure 2:
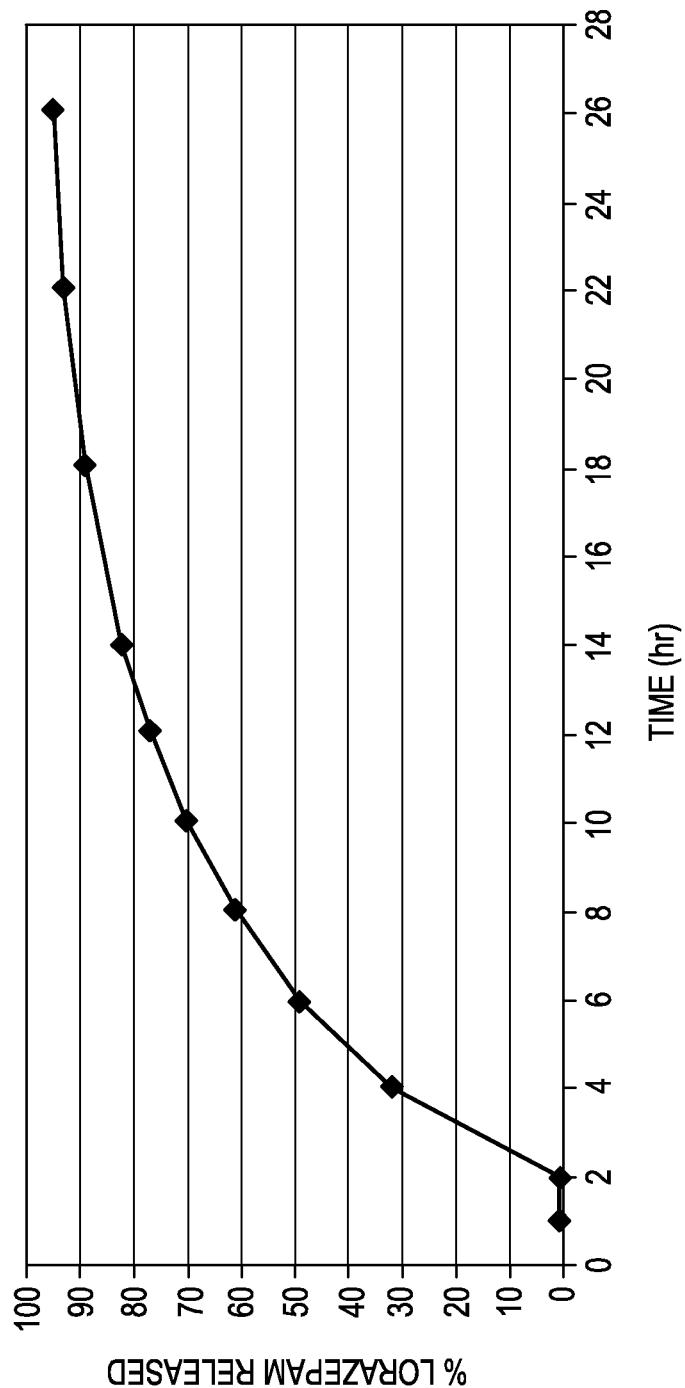
FIG. 2 represents the dissolution of the lorazepam delayed sustained release beads made in Example 2 in a two media dissolution test.

Samples of the delayed sustained release lorazepam beads were subjected to the two media in vitro dissolution test using pH 7.4 buffer media and the results are summarized below. The average result is graphically represented in FIG. 2.

| Apparatus | USP Apparatus 1 | Volume | 900 mL |
|---|---|---|---|
| Rotation Speed | 100 RPM | Temperature | 37° C. ± 0.5° C. |
| Medium | H 0-2: 0.1N HCl | Number of Units | 6 |
| | H 2-26: pH 7.4 Phosphate Buffer | | |

| | | Collection Time (h) | | | | | | | | | |
|---|---|---|---|---|---|---|---|---|---|---|---|
| | | 1 | 2 | 4 | 6 | 8 | 10 | 12 | 14 | 18 | 22 | 26 |
| Percent Dissolved | 1 | 28 | 41 | 56 | 65 | 72 | 78 | 83 | 89 | 90 | 91 | 91 |
| | 2 | 28 | 42 | 57 | 67 | 75 | 80 | 85 | 86 | 93 | 94 | 94 |
| | 3 | 28 | 40 | 56 | 65 | 72 | 78 | 83 | 89 | 90 | 92 | 92 |
| | 4 | 28 | 42 | 58 | 67 | 74 | 80 | 85 | 88 | 92 | 94 | 94 |
| | 5 | 29 | 42 | 59 | 68 | 76 | 82 | 87 | 90 | 94 | 96 | 96 |
| | 6 | 29 | 43 | 59 | 68 | 75 | 81 | 86 | 89 | 93 | 94 | 94 |
| | Mean | 28 | 42 | 58 | 67 | 74 | 80 | 85 | 88 | 92 | 94 | 94 |
| | RSD | 2.2 | 2.2 | 2.4 | 2.0 | 2.3 | 2.0 | 1.9 | 1.9 | 1.8 | 1.9 | 1.9 |

RSD = Relative Standard Deviation.

| Apparatus | USP Apparatus 1 | | | | | Volume | | 900 mL | | | |
|---|---|---|---|---|---|---|---|---|---|---|---|
| Rotation Speed | 100 RPM | | | | | Temperature | | 37° C. ± 0.5° C. | | | |
| Medium | H 0-2: 0.1N HCl | | | | | Number of | | 6 | | | |
| | H 2-26: pH 7.4 Phosphate Buffer | | | | | Units | | | | | |

| | | Collection Time (h) | | | | | | | | | |
|---|---|---|---|---|---|---|---|---|---|---|---|
| | | 1 | 2 | 4 | 6 | 8 | 10 | 12 | 14 | 18 | 22 | 26 |
| Percent | 1 | 1 | 2 | 34 | 52 | 64 | 73 | 80 | 86 | 93 | 97 | 99 |
| Dissolved | 2 | 0 | 1 | 31 | 48 | 59 | 68 | 75 | 81 | 88 | 97 | 95 |
| | 3 | 0 | 1 | 32 | 49 | 60 | 69 | 76 | 81 | 88 | 91 | 93 |
| | 4 | 1 | 1 | 33 | 51 | 62 | 71 | 78 | 83 | 89 | 92 | 93 |
| | 5 | 1 | 1 | 32 | 49 | 61 | 70 | 77 | 82 | 88 | 92 | 93 |
| | 6 | 1 | 1 | 32 | 50 | 62 | 71 | 78 | 83 | 91 | 95 | 97 |
| | Mean | 1 | 1 | 32 | 49 | 61 | 70 | 77 | 82 | 89 | 93 | 95 |
| | RSD | 27.0 | 20.6 | 3.2 | 3.0 | 2.9 | 2.5 | 2.3 | 2.3 | 2.3 | 2.4 | 2.7 |

RSD = Relative Standard Deviation.

Figure 3:
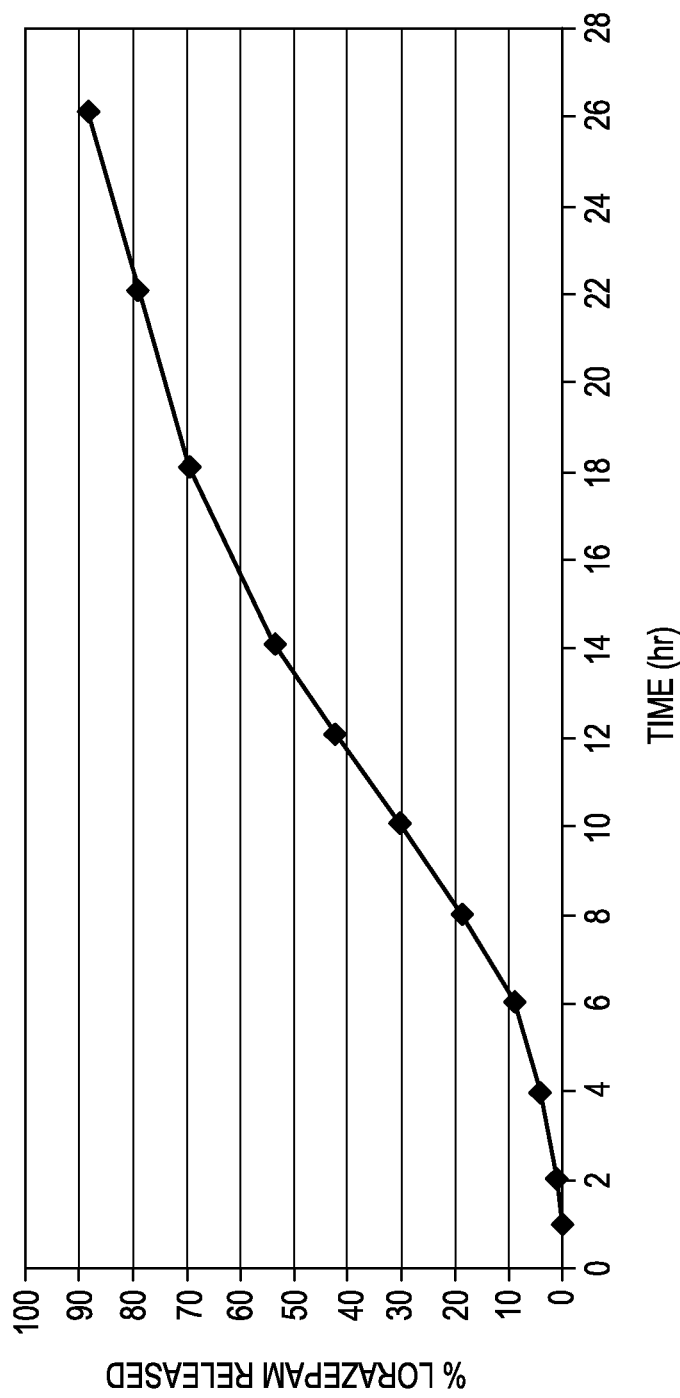
FIG. 3 represents the dissolution of the lorazepam delayed sustained release beads of Example 2 using a different two media dissolution test wherein the second media has a pH of 6.8 instead of 7.4.

For comparison, samples of the delayed sustained release beads were subjected to a modified two media in vitro dissolution test where the pH 7.4 buffer media was replaced with a pH 6.8 buffer media. The results are summarized below and the average is graphically shown in FIG. 3.

| Apparatus | USP Apparatus 1 | | | | | Volume | | 500 mL | | | |
|---|---|---|---|---|---|---|---|---|---|---|---|
| Rotation Speed | 100 RPM | | | | | Temperature | | 37° C. ± 0.5° C. | | | |
| Medium | H 0-2: 0.1N HCl | | | | | Number of | | 6 | | | |
| | H 2-26: pH 6.8 Phosphate Buffer | | | | | Units | | | | | |

| | | Collection Time (h) | | | | | | | | | |
|---|---|---|---|---|---|---|---|---|---|---|---|
| | | 1 | 2 | 4 | 6 | 8 | 10 | 12 | 14 | 18 | 22 | 26 |
| Percent | 1 | 0 | 1 | 4 | 11 | 21 | 33 | 46 | 57 | 73 | 83 | 92 |
| Dissolved | 2 | 0 | 1 | 3 | 8 | 17 | 28 | 40 | 51 | 67 | 78 | 87 |
| | 3 | 0 | 1 | 4 | 10 | 20 | 30 | 42 | 53 | 68 | 79 | 87 |
| | 4 | 0 | 1 | 4 | 9 | 19 | 30 | 42 | 53 | 69 | 80 | 88 |
| | 5 | 0 | 1 | 4 | 9 | 18 | 28 | 40 | 51 | 67 | 77 | 85 |
| | 6 | 0 | 1 | 3 | 9 | 18 | 29 | 41 | 52 | 67 | 79 | 87 |
| | Mean | 0 | 1 | 4 | 9 | 19 | 30 | 42 | 53 | 69 | 79 | 88 |
| | RSD | 13.5 | 17.8 | 16 | 11.6 | 7.8 | 6.8 | 5.1 | 4.4 | 3.2 | 2.7 | 2.6 |

RSD = Relative Standard Deviation.

As can be seen from the above results, the delayed sustained release beads showed a significant reduction in the amount released at hours 4 and 6 in the pH 6.8 buffer in comparison to the pH 7.4 buffer used in the two media test dissolution test.

Example 3

A pharmaceutical composition containing sustained release lorazepam beads and delayed sustained release lorazepam beads was formed by filling a capsule with the beads of Examples 1 and 2. A hard gelatin capsule was filled with the following nominal amounts of ingredients to form a 2 mg lorazepam oral dosage form.

| Component | Reference to Quality Standards | Function | Unit Composition | |
|---|---|---|---|---|
| | | | mg/Unit | % w/w |
| Example 1 beads | | | 33.33 | 45.09% |
| Example 2 beads | | | 40.60 | 54.91% |

-continued

| Component | Reference to Quality Standards | Function | Unit Composition | |
|---|---|---|---|---|
| | | | mg/Unit | % w/w |
| Hard gelatin capsule shell | | Capsule | 1 unit | — |
| Total | | | 73.93 | 100.0 |

[a] = 2 mg Lorazepam dose. The contribution is 50% from the Example 1 beads and 50% from the Example 2 beads.

The nominal 2 mg lorazepam capsules were evaluated in a single dose pharmacokinetic study involving 24 subjects. The dose was administered under fasting conditions. The study lasted for 120 hours. The study average showed that lorazepam was being absorbed beyond 30 hours. The calculated steady state values show that therapeutic concentrations of lorazepam are maintained over a 24 hour period by once daily dosing of the 2 mg lorazepam capsules of the invention. The steady state Cmax and Cmin are each about equal to the corresponding Cmax and Cmin achieved with a b.i.d. dosing regimen of 1 mg immediate release lorazepam tablets (1 mg per 12 hours equals 2 mg per day).

Each of the patents and articles mentioned above are incorporated herein by reference. The invention having been described it will be obvious that the same may be varied in many ways and all such modifications are contemplated as being within the scope of the invention as defined by the following claims.

We claim:

1. A pharmaceutical composition, comprising (i) lorazepam sustained release beads and (ii) lorazepam delayed sustained release beads, wherein the total amount of lorazepam contained in said composition is 0.5 mg to 10 mg and wherein said composition when administered once daily provides (1) a lorazepam blood plasma steady state Cmax that is +/−35% of the Cmax achieved by immediate release tablets given twice daily and having the same total daily amount of lorazepam, and/or (2) a lorazepam blood plasma steady state Cmin that is +/−35% of the Cmin achieved by immediate release tablets given b.i.d. and having the same total daily amount of lorazepam.

2. The pharmaceutical composition according to claim 1, wherein said composition, when administered once daily to a patient, maintains a therapeutic effect for at least 24 hours.

3. The pharmaceutical composition according to claim 1, wherein 100% of the lorazepam in said composition is contained in the combination of said sustained release beads and said delayed sustained release beads.

4. The pharmaceutical composition according to claim 1, wherein said sustained release beads have a dissolution profile in a two media in vitro dissolution test such that from 20 70% of the lorazepam is released in 2 hours; and wherein said two media in vitro dissolution test is carried out for two hours in a media that comprises 0.1 N HCl and then is carried out in a media that comprises a phosphate buffer and has a pH of 7.4.

5. The pharmaceutical composition according to claim 4, wherein said dissolution profile further includes the release of 50% of the lorazepam within 1 to 5 hours.

6. The pharmaceutical composition according to claim 4, wherein said dissolution profile further includes that 90% of the lorazepam is not released before 10 hours.

7. The pharmaceutical composition according to claim 1, wherein said lorazepam delayed sustained release beads have a dissolution profile in a two media in vitro dissolution test such that the release of 90% of the lorazepam occurs after 10 hours; and wherein said two media in vitro dissolution test is carried out for two hours in a media that comprises 0.1 N HCl and then is carried out in a media that comprises a phosphate buffer and has a pH of 7.4.

8. The pharmaceutical composition according to claim 1, wherein said delayed sustained release beads contain a delay coating that is pH-dependent and wherein said delayed sustained release beads have a dissolution profile in a two media in vitro dissolution test such that from 20 80% of the lorazepam is released in 4 hours; and wherein said two media in vitro dissolution test is carried out for two hours in a media that comprises 0.1 N HCl and then is carried out in a media that comprises a phosphate buffer and has a pH of 7.4.

9. The pharmaceutical composition according to claim 1, wherein said sustained release beads comprise lorazepam dispersed in a polymer matrix and wherein said delayed sustained release beads comprise a core having lorazepam dispersed in a polymer matrix and an enteric coating surrounding said core.

10. The pharmaceutical composition according to claim 2, wherein said sustained release beads comprise lorazepam dispersed in a polymer matrix and wherein said delayed sustained release beads comprise a core having lorazepam dispersed in a polymer matrix and an enteric coating surrounding said core.

11. The pharmaceutical composition according to claim 9, wherein said polymer matrix in the sustained release beads and in the delayed sustained release beads comprises hydroxypropyl methylcellulose (HPMC).

12. The pharmaceutical composition according to claim 11, wherein said enteric coating is designed to release a drug at pH 7 or greater.

13. The pharmaceutical composition according to claim 1, wherein said composition provides, when dosed once daily, a lorazepam blood plasma steady state Cmax of not greater than 12 ng/ml for each 1 mg of lorazepam, and/or a lorazepam blood plasma steady state Cmin of at least 5 ng/ml for each 1 mg of lorazepam.

14. The pharmaceutical composition according to claim 1, wherein said composition when administered once daily provides (1) a lorazepam blood plasma steady state Cmax that is +/−20% of the Cmax achieved by immediate release tablets given twice daily and having the same total daily amount of lorazepam, and/or (2) a lorazepam blood plasma steady state Cmin that is +/−20% of the Cmin achieved by immediate release tablets given b.i.d. and having the same total daily amount of lorazepam.

15. The pharmaceutical composition according to claim 1, wherein said composition exhibits continued release of lorazepam for at least 24 hours, as determined in single dose pharmacokinetic study.

16. A sustained release lorazepam pharmaceutical composition, which comprises lorazepam prolonged release beads, wherein said composition has a single dose pharmacokinetic profile that comprises a $T_{max}$ at 4 hours or longer and continued release of lorazepam beyond 20 hours; and wherein said composition being an oral dosage form containing from 0.5 mg to 10 mg of lorazepam and when administered once daily to a patient maintains a therapeutic effect for at least 24 hours.

17. The composition according to claim 16, wherein said pharmacokinetic profile includes the continued release of lorazepam for at least 24 hours.

18. The composition according to claim 17, wherein said pharmacokinetic profile includes the continued release of lorazepam for at least 28 hours.

19. The composition according to claim 16, wherein said pharmacokinetic profile provides during 0-24 hours from 40 to 60% of AUC during 0-120 hours.

20. A method for treating a lorazepam-treatable condition in a patient, which comprises administering once a day to a patient in need thereof a pharmaceutical composition according to claim 1 in a sufficient dose to provide 24 hour therapeutic effect during steady state conditions.

* * * * *